(12) United States Patent
Heuser

(10) Patent No.: US 6,464,665 B1
(45) Date of Patent: Oct. 15, 2002

(54) CATHETER APPARATUS AND METHOD FOR ARTERIALIZING A VEIN

(76) Inventor: Richard R. Heuser, 2626 E. Arizona Biltmore Cir., No. 9, Phoenix, AZ (US) 85016

( * ) Notice: Subject to any disclaimer, the term of this patent is extended or adjusted under 35 U.S.C. 154(b) by 44 days.

(21) Appl. No.: 09/609,992

(22) Filed: Jul. 5, 2000

(51) Int. Cl.$^7$ .......................... A61M 29/00; A61B 17/22
(52) U.S. Cl. ............... 604/104; 604/96.01; 604/101.01; 606/159
(58) Field of Search .................. 604/96.01, 101.01, 604/101.03, 101.05, 104–109; 606/159, 167, 189, 194; 623/1.11, 1.12, 1.15, 1.2, 1.36

(56) References Cited

U.S. PATENT DOCUMENTS

| | | | | |
|---|---|---|---|---|
| 4,650,466 A | * | 3/1987 | Luther | 604/95 |
| 5,112,310 A | * | 5/1992 | Grobe | 604/175 |
| 5,743,900 A | | 4/1998 | Hara | |
| 5,830,222 A | | 11/1998 | Makower | |
| 5,830,224 A | | 11/1998 | Cohn et al. | |
| 5,868,708 A | * | 2/1999 | Hart et al. | 604/104 |
| 5,928,260 A | * | 7/1999 | Chin et al. | 606/200 |
| 5,944,019 A | * | 8/1999 | Knudson et al. | 128/898 |
| 5,968,064 A | * | 10/1999 | Selmon et al. | 606/189 |
| 5,976,178 A | | 11/1999 | Goldsteen et al. | |
| 6,030,406 A | * | 2/2000 | Davis et al. | 606/198 |
| 6,071,292 A | * | 6/2000 | Makower et al. | 606/158 |

OTHER PUBLICATIONS

A. M. A. Archives of Surgery: Femoral Arteriovenous Anastomosis in the Treatment of Occlusive Arterial Disease, undated.

Arteriovenous Anastomosis—Reversal of the Circulation—As a Preventive of Gangrene of the Extremities by Bertram M. Bernheim, M.D., undated.

Surgery, Gynecology and Obstetrics: Arteriovenous Anastomosis in the Treatment of Gangrene of the Extremities. Jan. 1912.

Surgery: Collateral Circulation in the Presence of Experimental Arteriovenous Fistula. Jan. 1950.

JAMA: Effects of an Arteriovenous Fistula on the Devascularized Limb. Feb. 22, 1965.

(List continued on next page.)

Primary Examiner—Sharon Kennedy
(74) Attorney, Agent, or Firm—Kolisch Hartwell

(57) ABSTRACT

A catheter apparatus is provided including an arterial catheter and a venous catheter wherein the distal ends of the catheter are insertable in an artery and a adjacent vein, respectively to a position adjacent a site for creating a fistula. The venous catheter includes a radially expandable structure adjacent the distal end which can be selectively extended outwardly to expand a portion of the wall of the vein adjacent the venous fistula site towards contact with the wall of the artery adjacent the arterial fistula site. The radially expandable structure of the venous catheter may include one or more balloons which can be inflated or a wire basket, or the vein can be expanded by injecting a fluid through an injection port into an isolated portion of the vein. The apparatus further includes a tool for creating an opening through the wall of the artery adjacent the arterial fistula site and an opening through the outwardly extending portion of the wall of the vein adjacent the venous fistula site to extend outwardly the portion of the wall of the vein towards contact with the wall of the artery. The tool may include a needle coupled to the arterial catheter adjacent the distal end of the arterial catheter, the needle being selectively switchable between a first, inactive configuration wherein the needle can be guided through the artery without causing trauma to the artery wall and a second, active configuration wherein the needle is operative to create the opening in the artery wall. The fistula between the openings may be completed with the aid of a stent, and the proximal portion of the vein blocked with an embolization device.

27 Claims, 8 Drawing Sheets

OTHER PUBLICATIONS

American Journal of Surgery: Revascularization of Severely Ischemic Extremities with an Arteriovenous Fistula. Aug. 1966.

Basic Research in Cardiology: Collateral vessel formation: isolation of a transferable factor promoting a vascular response. Jan. 9, 1975.

Ann. Surg.: Use of an Arteriovenous Fistula for Treatment of the Severely Ischemic Extremity: Experimental Evaluation. Nov. 1976.

Br. J. Surg.: Treatment of critical ischaemia of the lower limb by venous arterialization: an interim report. 1977.

Surgery: Acute physiologic effects of arteriovenous anastomosis and fistula in revascularizing the ischemic canine hind limb. Apr. 1981.

JAMA: Lipid Angiogenic Factor from Omentum. Oct. 19, 1984.

The Lancet: Angiogenesis Factor for Human Myocardial Infarcts. Aug. 13, 1983.

Surgery, Gynecology & Obstetrics: An Angiographic Study of Ischemia as a Determinant of Neovascularization in Arteriovenous Reversal. Jan. 1988.

* cited by examiner

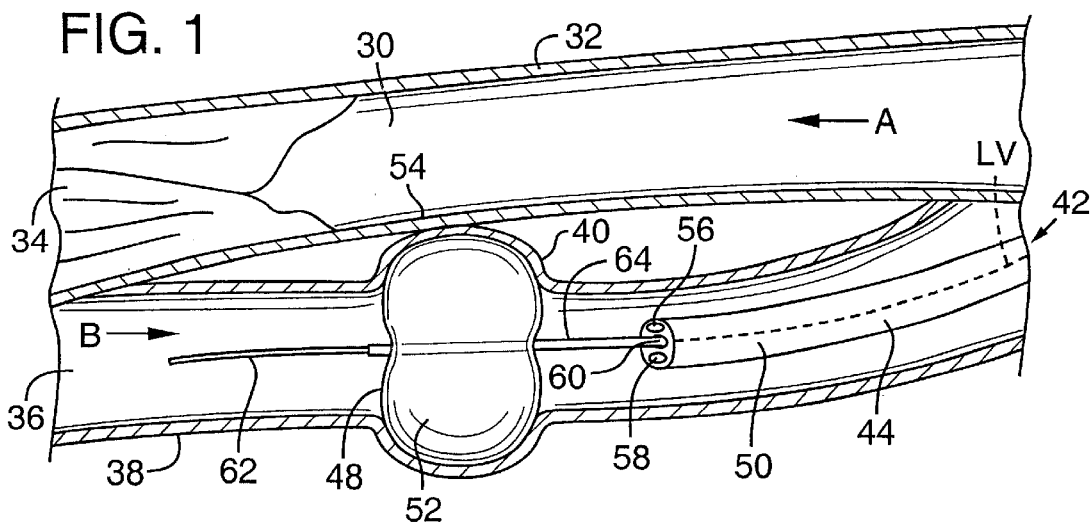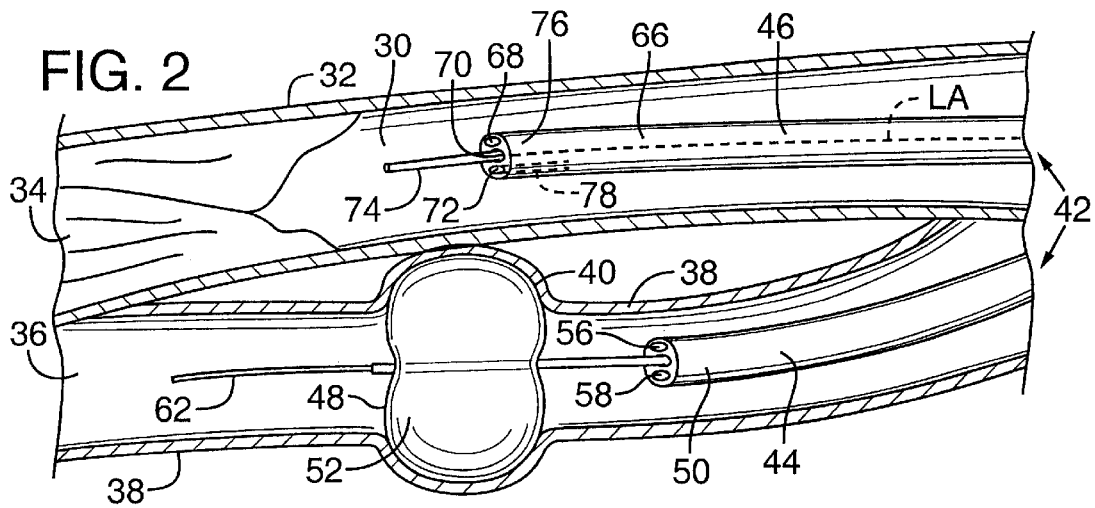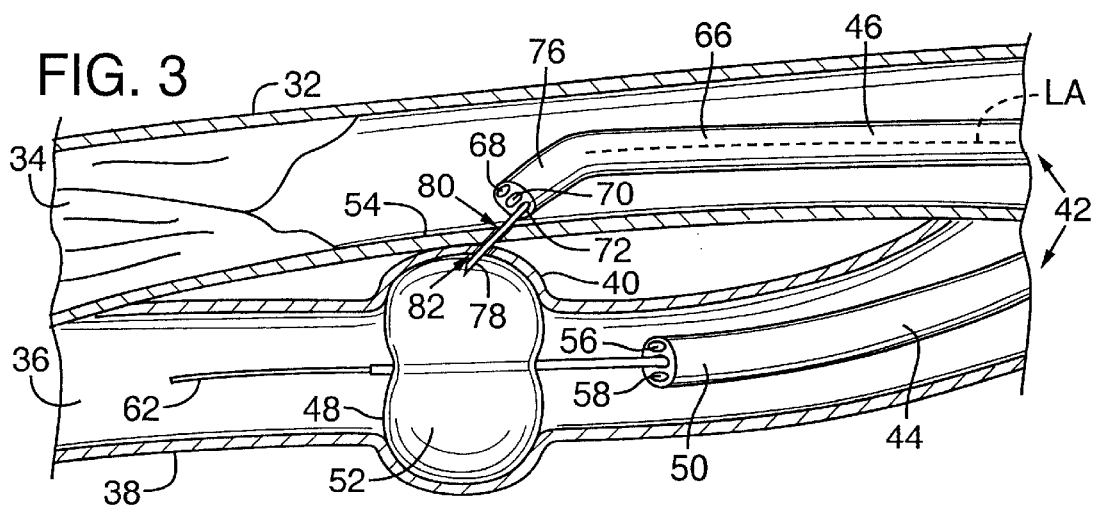

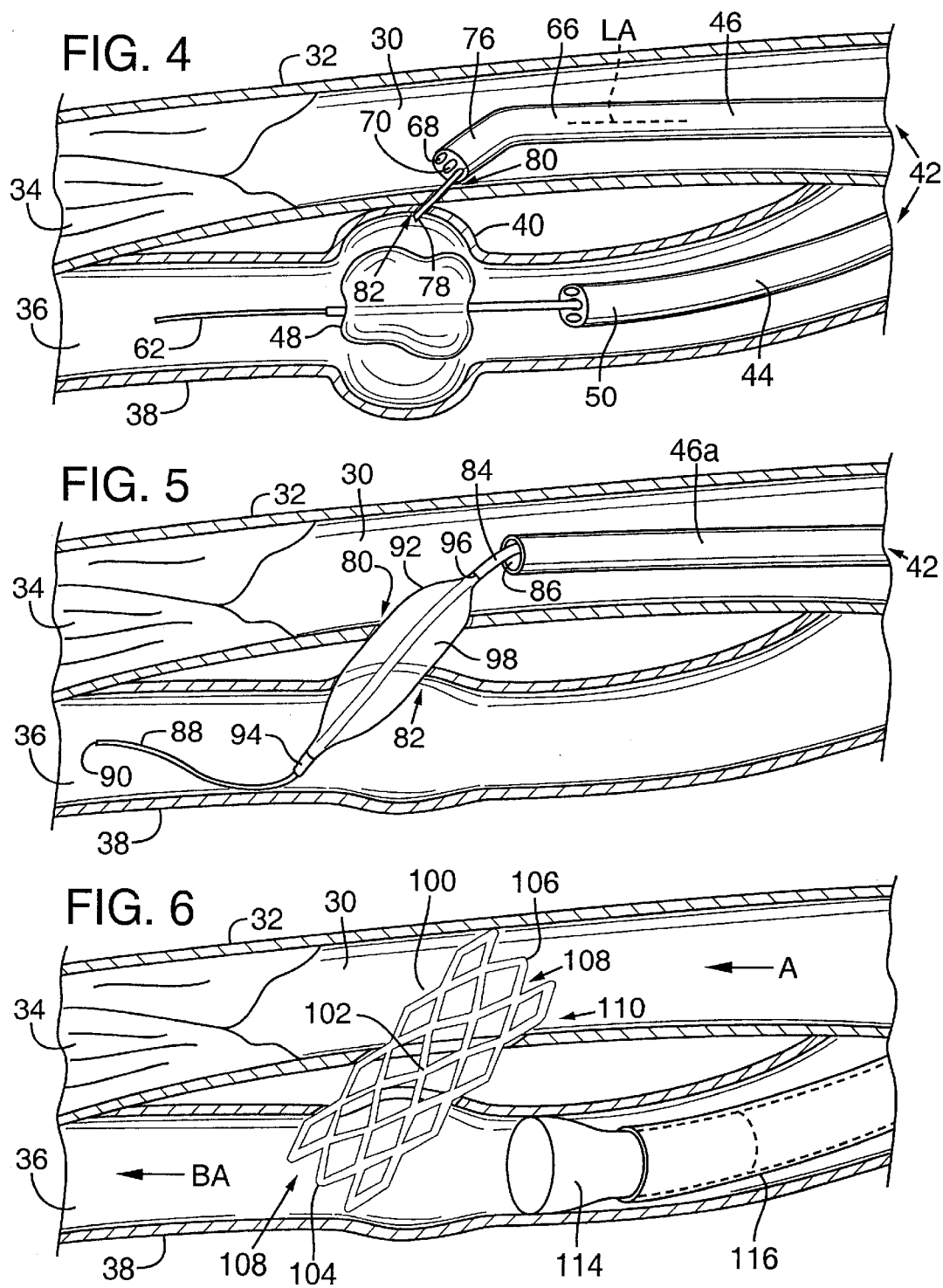

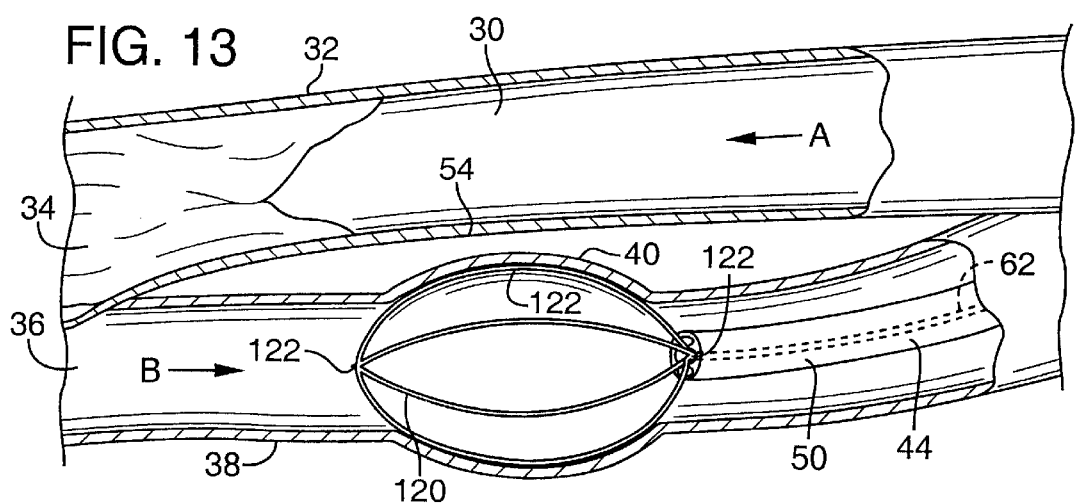
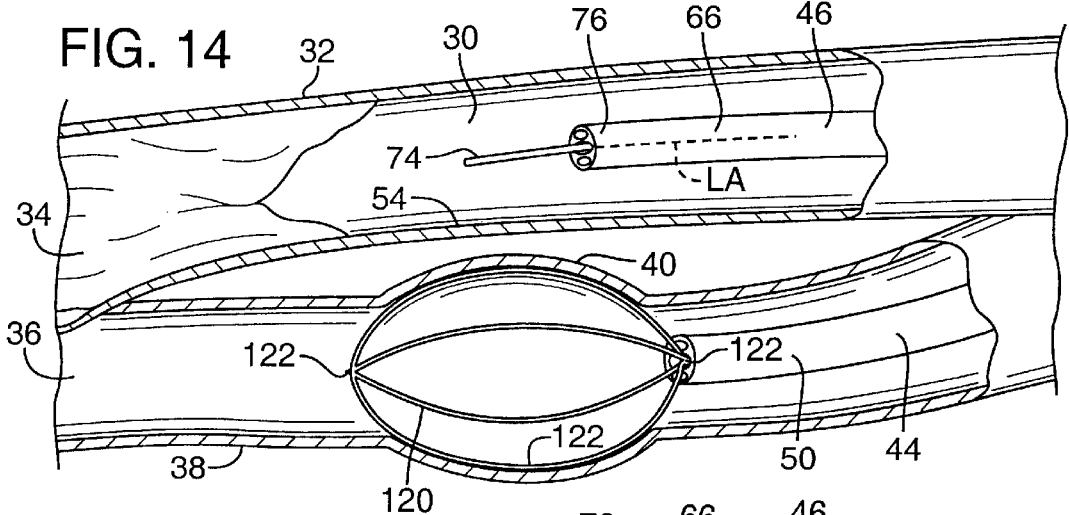
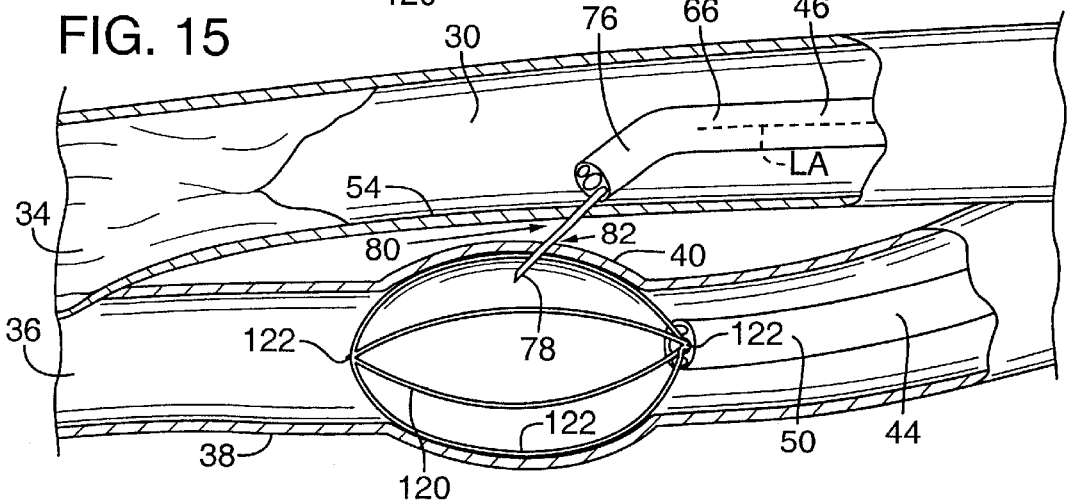

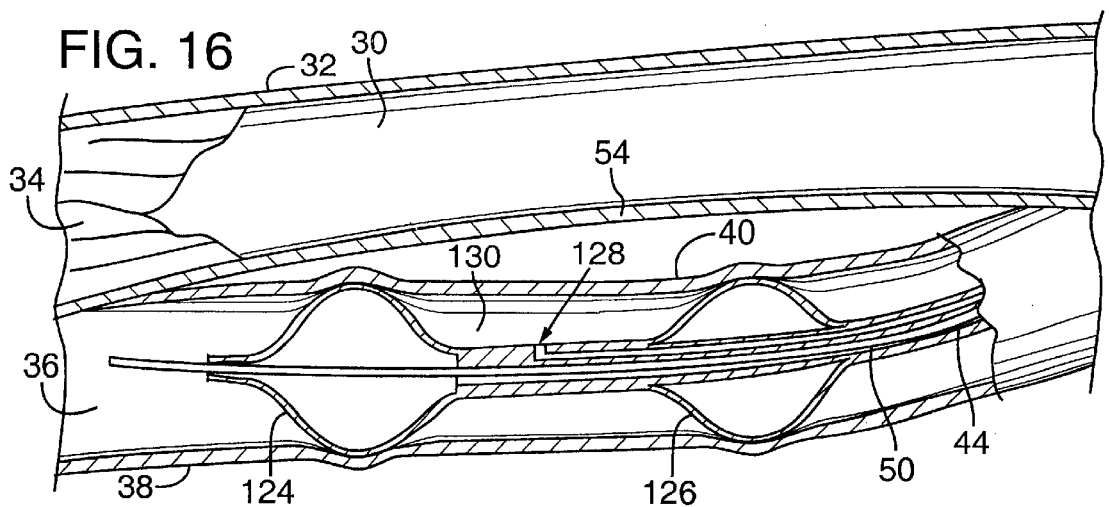
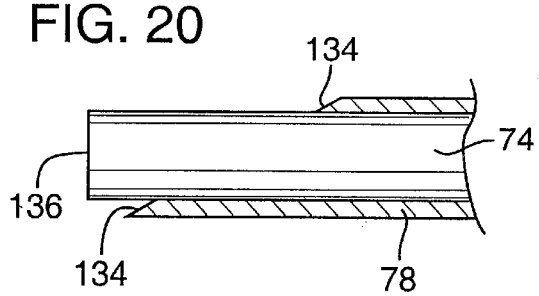 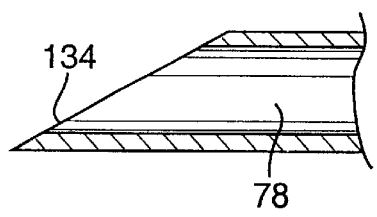

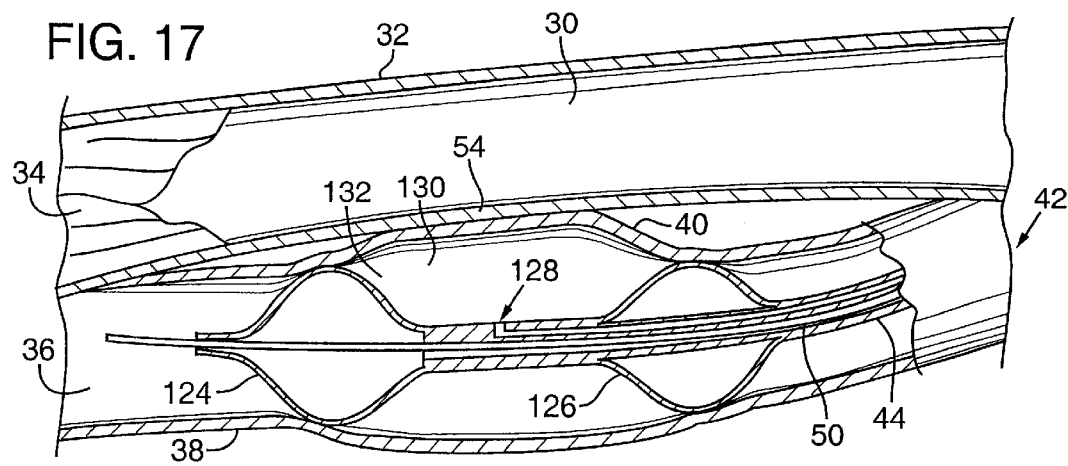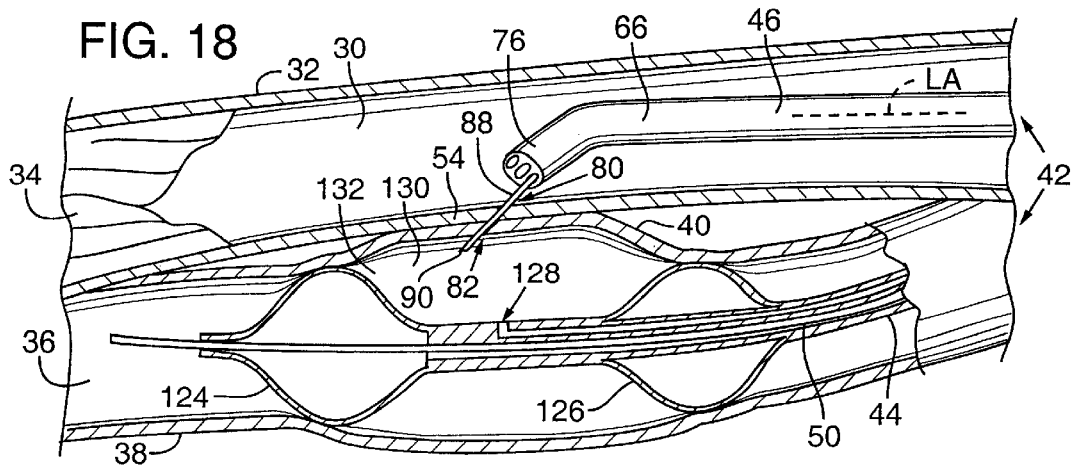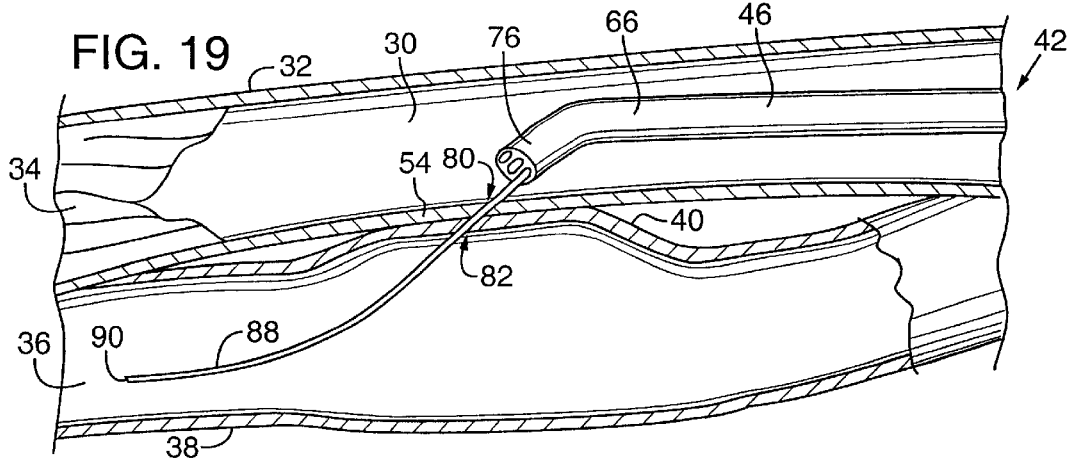

CATHETER APPARATUS AND METHOD FOR ARTERIALIZING A VEIN

BACKGROUND

This invention relates generally to an apparatus and method for converting a vein for arterial blood flow. More particularly the invention concerns an apparatus and method for expanding a portion of the vein in an area adjacent to an occluded artery, creating an opening through the artery wall and through the expanded portion of the vein wall, creating a fistula between the two openings for blood flow from the artery to the vein, and creating a stationary embolism in the vein proximal to the opening to prevent direct return of the blood to the heart.

The superficial femoral arteries and the popliteal arteries are leg arteries that provide blood flow through the legs and to the feet, particularly to the skin and areas just below the skin. Patients suffering from partial or complete occlusions in such arteries typically experience claudication, i.e., leg pain or limping while walking, and difficulty in healing wounds on the legs due to ischemia, although the deep femoral artery may provide enough circulation that at least the pain is reduced by resting. However, standard open bypass often is impossible on such patients, particularly those with diabetes-narrowed arteries, because of the substandard ability to heal the necessary incisions. Performing angioplasty or inserting stents are unlikely to help where the vessels are too small or the occlusion extends all the way down to the foot. In severe cases, non-healing ulcers or resting pain may leave no alternative except amputation. Thus, peripheral vascular disease presents a serious health risk not adequately addressed by prior means and methods of intervention.

SUMMARY OF THE INVENTION

The invented device and method provides for arterializing a peripheral vein lying alongside an artery that is not allowing sufficient blood flow. The complexly branched structure of peripheral veins typically provide more than enough paths for blood flow back to the heart, and thus switching a vein to arterial blood flow may allow sufficient venous blood flow through other veins. The arterialized vein improves arterial blood flow to the fine network of capillaries that the vein formerly drained and, if reconnected, to the artery distal to the occlusion. This results in improved ability to heal wounds and reduced ischemia and claudication. Typically, a vein that is a candidate for arterialization lies roughly parallel and in proximity to the occluded artery, but some distance may separate the vein from the artery in a desired site for creating a fistula proximal to the occlusion.

According to the invention, in a patient having peripheral vascular disease resulting in a partial or total occlusion of a peripheral artery, an angiogram is performed to map the occlusion in the artery and a venogram is performed using a catheter inserted in a parallel, candidate vein from the foot or contra-laterally via the inferior vena cave The venogram catheter is used to inject contrast and thus to map the size and branches of the vein and its proximity to the occluded artery, particularly in an area proximal to the arterial occlusion where the arterial-venous (AV) fistula can be created. The amount of run-off, i.e., venous blood flow, is also assessed to determine the potential downside of arterializing the vein.

Once the vein and the sites for the fistula in the vein and the artery are selected, a venous-expansion catheter that includes a structure for selectively extending outwardly the vein wall is inserted percutaneously into the vein and the structure is maneuvered into position adjacent the venous side of the fistula site. Another catheter is inserted percutaneously into the artery, this catheter including a tool at its distal end capable of creating an opening through the arterial wall and the venous wall. With both catheters in place, the venous-expansion catheter is used to expand the venous wall adjacent the fistula site until the wall touches or at least comes in closer proximity to the arterial wall. Proximity of the walls as well as expansion of the venous wall may also be promoted by attraction between magnetic devices disposed on the catheters. Then, the arterial catheter tool is used to create an opening in the vein and an opening in the artery in close enough proximity that a fistula between the vein and artery can be completed.

The openings may be widened, if necessary, by balloon angioplasty. A stent, or other device for maintaining blood flow through the openings and preventing blood leakage between the vessels, is then inserted through the openings in a compressed state. The stent may include small, radiopaque hooks on each end that embed in the inner walls of the vein and artery. As the stent reverts from a narrowed, lengthened configuration, produced by compression in an insertion device, to its nominal shortened, widened configuration, the hooks pull the vein and artery tightly together, even invaginating the vein into the artery or the artery into the vein. The position of the hooks can be observed radiographically to gauge the connection between the vessels.

Thus, the vein is arterialized, i.e., it receives arterial blood flow in the reverse direction of its previous venous flow. Then, the vein is blocked by depositing a device in the vein proximal to the fistula, either using the original venous-expansion catheter or by a separate thrombus-insertion catheter, in order to promote arterial blood flow to the smaller vessels formerly drained by the vein and to prevent the vein from simply providing a conduit from the fistula back to the heart. Under some circumstances, the vein may be reconnected to the artery distal of the occlusion using a method and apparatus similar to that described above and below for the AV fistula, although such reconnection is often not necessary, and may not be possible in the case of lengthy occlusions. In the case of reconnection of the vein to the artery, a thrombotic device will typically be used to close off the vein distal of the reconnection to the artery. Branches of the vein that lead to areas that are already well-served with arterial circulation, whether or not the vein is reconnected, will be occluded with thrombotic material.

After creation of the fistula and the proximal closing of the vein, an angiogram is performed to assess run-off, and the patient may be helped by the wearing of fill-length support hose to promote run-off. The success of the arterialization is gauged by the patient's improvement in claudication and ischemia, as well as the increase in the ratio of blood pressure at the ankle to blood pressure at the upper arm, known as ankle-to-brachial index or ABI.

To prevent valves in the arterialized vein from impeding reverse blood flow, a cutting catheter, such as the TECT™ System by InterVentional Technologies, Inc. of San Diego, Calif. or the Rotoblader™, can be operated in the vein to disable the valves distal to the fistula site. The cutting catheter can be passed into the vein either as part of the venous-expansion catheter or separately through the same route as the venous-expansion catheter before the vein is closed off, or as part of the arterial catheter or along the same route through the fistula.

BRIEF DESCRIPTION OF THE DRAWINGS

FIG. 1 is a partial cross-sectional view of the present invention showing an occluded artery, including the occlusion and the area proximal to the occlusion, i.e., closer to the heart, and a vein alongside the artery, the vein including a portion which has been extended outwardly by inflation of a balloon on a three-lumen catheter inserted into the vein, an outer surface of the vein being moved by the radial expansion of the balloon closer to, and into contact with an outer surface of the artery. FIG. 1 is the first in a series of six figures (FIGS. 1–6) showing a set of steps to accomplish an embodiment of the invented method, the figures all showing the vein and artery in cross-section and the instruments inserted therein in solid side or isometric views.

FIG. 2 is a cross-sectional view of the catheter with the balloon inflated in the vein as shown in FIG. 1, and an arterial catheter having three lumens inserted in the artery, one of the lumens having a stiffening guidewire extending beyond a distal end of the catheter to maintain the guidewire in a configuration wherein a distal tip of the catheter is generally aligned with a longitudinal axis of the main body of the catheter, another of the lumens having a needle stored therewithin in an inactive configuration.

FIG. 3 is a cross-sectional view of the vein, artery, and two catheters, the arterial catheter shown with the stiffening wire withdrawn from the distal tip, and the distal tip shown in a configuration wherein it is offset by about 30° from the longitudinal axis of the arterial catheter, and a sharp wire or needle extending from the tip and into the walls of the artery and vein to create openings through the artery and vein walls for connection of a fistula between the artery and the vein.

FIG. 4 is a cross-sectional view of the vein, artery, and two catheters with the needle or sharp wire of the arterial catheter having just punctured the balloon after creating the opening through the vein wall, and the balloon deflating.

FIG. 5 is a cross-sectional view of a balloon catheter inserted into the artery with the balloon disposed through and inflated within the openings in the vein and artery walls, enlarging the openings.

FIG. 6 is a cross-sectional view of a stent in place between the artery and vein to maintain the fistula open and a thrombotic device being ejected from a catheter as the catheter is withdrawn, the thrombotic device lodging in the vein proximal to the fistula to prevent blood flow toward the heart via the vein.

FIG. 13 is a partial cross-sectional view of an embodiment of the present invention showing an occluded artery, including the occlusion and the area proximal to the occlusion and a vein alongside the artery, the vein including a portion which has been extended outwardly by expansion of a wire basket on a three-lumen catheter inserted into the vein, an outer surface of the vein being moved by the radial expansion closer to an outer surface of the artery.

FIG. 14 is a partial cross-sectional view of the catheter with the wire basket expanded in the vein as shown in FIG. 13, and an arterial catheter having three lumens inserted in the artery, one of the lumens having a stiffening guidewire extending beyond a distal end of the catheter to maintain the guidewire in a configuration wherein a distal tip of the catheter is generally aligned with a longitudinal axis of the main body of the catheter.

FIG. 15 is a partial cross-sectional view of the vein, artery, and two catheters, the arterial catheter shown with the stiffening wire withdrawn from the distal tip, and the distal tip shown in a configuration wherein it is offset by about 30° from the longitudinal axis of the arterial catheter, and a sharp wire or needle extending from the tip and through the walls of the artery and vein to create openings through the artery and vein walls for connection of a fistula between the artery and the vein.

FIG. 16 is a cross-sectional view of an embodiment of the present invention showing a pair of longitudinally spaced balloons on the venous catheter, the balloons inflated to create an isolated area therebetween and also showing an injection port on the venous catheter in communication with the isolated area.

FIG. 17 is a cross-sectional view of the embodiment of FIG. 16 showing the wall of the vein extended outwardly, adjacent the isolated area between the balloons, due to injection of a substance through the injection port FIG. 18 is a cross-sectional view of the embodiment of FIGS. 16 and 17, further showing the arterial catheter with the sharp-tipped wire extending therefrom creating openings through the vein and artery walls.

FIG. 19 is a cross-sectional view of the embodiments of FIGS. 16–18, further showing the sharp-tipped wire extended through the openings in the artery and vein walls and into and along the vein.

FIG. 20 is a cross-sectional view of the needle of FIGS. 3 and 4 wherein the needle is hollow and has a tip made pointed by a beveled cut, and the needle is made inactive by a blunt-tipped wire inserted therethrough to a position beyond the needle tip.

FIG. 21 is a cross-sectional view of the needle of FIG. 20 wherein the needle is made active for piercing by withdrawal of the wire to expose the bevel-pointed tip.

DETAILED DESCRIPTION OF THE PREFERRED EMBODIMENTS

Figure 5A:
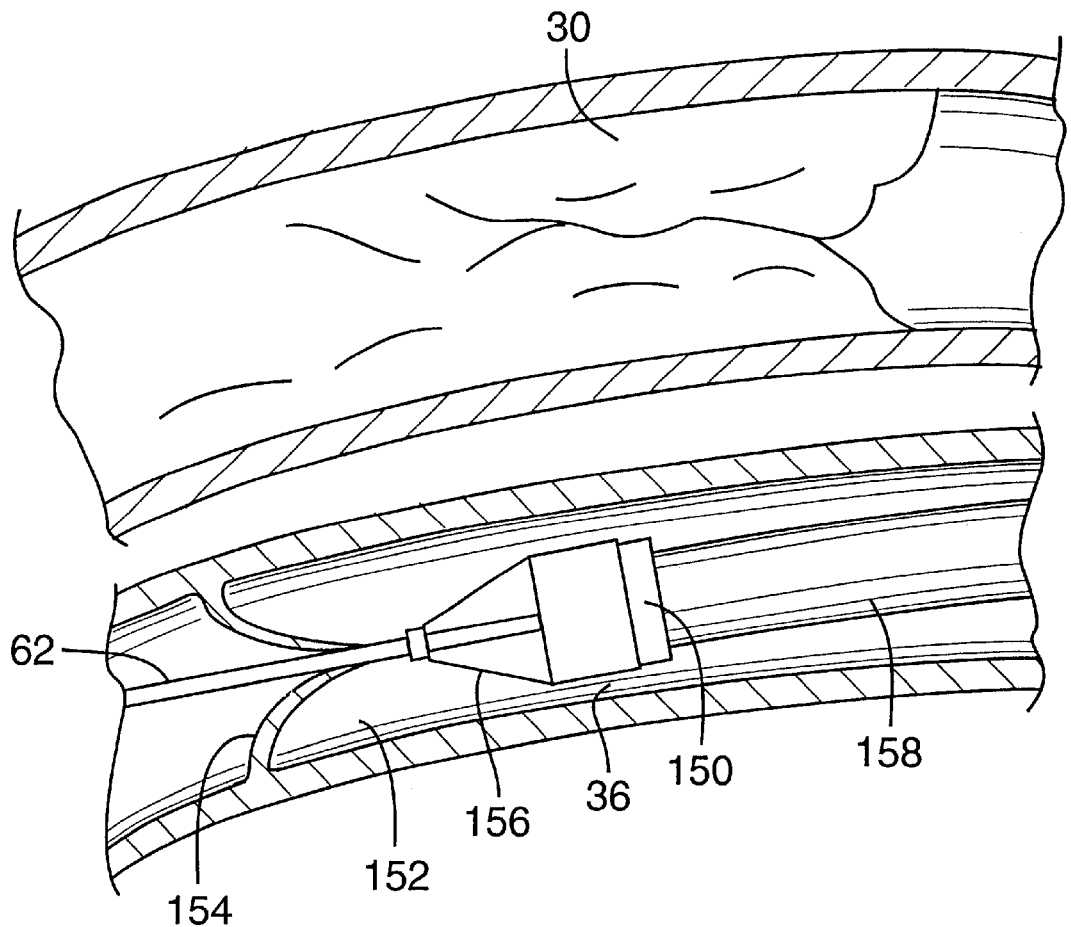
FIG. 5a is a cross-sectional view of a cutting catheter about to cut through and remove by vacuum extraction a valve in the vein distal to the fistula site.

As shown in FIG. 1, an artery 30, formed by an artery wall 32, has a blood flow, indicated by arrow A, partially or totally blocked by an occlusion 34, typically formed by plaque. A vein 36 roughly similar in dimension to artery 30 lies alongside and generally parallel to artery 30. Vein 36, formed by a vein wall 38, includes, in the area proximal to occlusion 34, a portion 40 in close proximity to artery 30 that the physician has selected as a venous site for creating a fistula between artery 30 and vein 36. The normal blood flow through vein 36 would be in the direction indicated by arrow B.

The invented device, indicated generally at 42 in FIG. 2, is a catheter apparatus that includes a venous catheter 44 and an arterial catheter 46. Venous catheter 44 includes a radially expandable structure, such as balloon 48, disposed adjacent a distal end 50 of venous catheter 44. Balloon 48 is selectively expandable by inflating, typically with a solution including a radiopaque dye or contrast 52. Radiographic markers adjacent the balloon may be used to check the position of the balloon before, during and after inflation. When expanded at venous fistula site 40 in vein 36, balloon 48 causes vein wall 38 to extend outwardly towards contact with wall 32 of artery 30 adjacent a site 54 within the artery selected for the fistula. The physician can radiographically observe contrast 52 in balloon 48 to judge the position and efficacy of the expansion of vein 36.

Venous catheter 44, which may also be termed a venous-expansion catheter, typically includes three lumens 56, 58, 60, which run generally parallel to a longitudinal axis LV of catheter 44. Balloon 48 is mounted on a wire 62 inserted through lumen 58. Wire 62 is controllable by the physician in position relative to catheter 44. Inflation of balloon 48 is controlled through an inflation tube 64. Wire 62 may be a guidewire for catheter 44, or a separate guidewire may be used, with either of lumens 56 and 60 providing the channel for the separate guidewire. Lumens 56 and 60 may also be used as conduits for injection of contrast to perform a venogram or to otherwise monitor the position of distal end 50 of catheter 44.

As shown in FIG. 2, arterial catheter 46 of catheter apparatus 42 includes a distal end 66 that the physician inserts into artery 30 and positions adjacent arterial fistula site 54. Arterial catheter 46 includes three lumens 68, 70, 72, which run generally parallel to a longitudinal axis LA of catheter 46. Arterial catheter 46 at lumen 70 is guided along a guidewire 74 inserted into artery 30. Arterial catheter 46 is typically 3 French in size or smaller.

Guidewire 74, also referred to as a stiffening wire, selectively controls the position of a distal tip 76 of arterial catheter 46 relative to axis LA. When stiffening wire 74 extends beyond distal tip 76, as shown in FIG. 2, distal tip 76 is generally aligned with axis LA. When the physician withdraws stiffening wire 74 from tip 76, as shown in FIG. 3, tip 76 returns to its nominal position, which is typically at least about 30° offset from axis LA. Alternatively, offsets of about 60° or about 90° or more, or any position in between, may be used depending on the geometry of the fistula sites and the physician's preference. It will be understood that other control structure may be used to control the configuration of distal tip 76, e.g., heating and/or cooling of shape-memory devices. Guidewire 74 is typically between about 0.010-inches and about 0.035-inches in diameter.

A tool, such as sharp, bevel-tipped, hollow needle 78, is selectively deployed, as shown in FIGS. 3 and 4, to create an opening 80 through artery wall 32 adjacent arterial fistula site 54 and an opening through the outwardly extending portion of vein wall 38 adjacent venous fistula site 40. Needle 78 is shown in dotted line in FIG. 2 in an inactive configuration withdrawn in lumen 72 into distal tip 76 of arterial catheter 46. In the inactive configuration, needle 78 can be guided through artery 30 without causing trauma to artery wall 32, and when deployed in an active configuration, the physician can guide needle 78 to create respective openings 80 and 82 in artery wall 32 and vein wall 38. Needle 78 is typically deployed by the physician's operating a switch at a proximal end of catheter 46. Other tools can be used to create openings 80, 82, including an ultrasound device, a photo wire system, an RF wire, or other devices that can make puncture, pierce, cut or otherwise make their way through a blood vessel wall.

Needle 78 may also puncture balloon 48, potentially causing a deflation of the balloon as well as the expanded portion of the vein and leakage of contrast 52 into the vein, as shown in FIG. 4. Such deflation and leakage are not generally harmful, although the deflation may cause needle 78 to slip out of opening 82 in the vein. Alternative embodiments, described below, avoid such deflation.

As shown in FIG. 5, after creating openings 80, 82 with a tool such as needle 78, venous catheter 44 is withdrawn from the fistula site and a balloon catheter 84 may be inserted through openings 80, 82 and inflated to enlarge the openings. Balloon catheter 84 may have a larger diameter that requires insertion through an arterial catheter 46a having a larger, single lumen 86, as shown in FIG. 5, but alternatively, balloon catheter 84 may be inserted through an unused one of lumens 68, 70 or 72 of arterial catheter 46.

Alternatively, balloon catheter 84 may include the tool necessary to create openings 80, 82 in the vessel walls. For example, as shown in FIG. 5, balloon catheter 84 may include a leading wire 88 having a tip 90 that is sufficiently sharp to pierce the artery and vein walls to create openings 80, 82, in which case advancement of balloon catheter 84 through openings 80, 82 simply follows. Balloon 92 of balloon catheter 84 may include radiopaque markers, such as leading and trailing markers 94, 96, respectively, and may be inflated with a solution containing a radiopaque dye or contrast 98 to allow the physician to radiographically monitor and adjust the position of the balloon before, during, and after inflation.

As shown in FIG. 5a, a cutting catheter 150 may be inserted along guidewire 62 into vein 36 to a position 152 distal of openings 80, 82 where a valve 154 forms a part of vein 36. Most veins include one or more such valves, and they are particularly numerous in the legs, where the valves decrease the blood pressure necessary to pump blood from the feet back to the heart by opposing reverse flow of the blood in the veins. Cutting catheter 150 includes a cutting device, such as rotating blade 156, and a vacuum-extraction tube 158 for removing excised tissue, i.e., some or all of valve 154, and such other valves distal of the fistula as need to be removed. The TEC™ System made by InterVentional Technologies, Inc. of San Diego, Calif. is an example of an extraction catheter that can be used to disable the valves to promote arterialized blood flow. Depending on the pre-operative competency of the valves, they may or may not require disabling in this manner—the pressure of the arterialized blood flow may be enough to overcome the resistance of the valves. The cutting catheter may alternatively be inserted along guidewire 88 through artery 30 and through the fistula to position 152 and beyond.

As shown in FIG. 6, a device for maintaining an open, leak-free connection between openings 80 and 82, such as stent 100, is inserted through the openings. Stent 100 includes a frame 102 having two open ends 104 and 106 and a passageway 108 extending therebetween. With openings 80, 82 connected to form a fistula, indicated generally at 110, vein 36 is arterialized, and blood flows from artery 30 into vein 36 in the direction indicated by arrows A and BA.

Stent 100 is typically a self-expanding type, e.g., the in-coil variety, or a Smart™, Bard™, Vasocoil™, or Jomed™ stent. Stent frame 102 may be covered with a non-absorbable material 112 (see FIG. 10), such as Dacron™, PTFE, thrombotic jell or putty, in particular Onyx™ putty, and the stent may thus prevent venous blood flow proximal to the fistula. Further aspects of the stent of the present invention are described below with reference to FIGS. 7 and 10–12.

As shown in FIG. 6, it may be desirable to close off venous blood flow in vein 36 proximal to fistula site 110, i.e., at a position that would be downstream from fistula site 110 under normal venous blood flow conditions. A thrombotic device 114 may be inserted in vein 36, typically by ejection from a thrombus-insertion catheter, which can be either venous-expansion catheter 44, or a separate catheter 116 as shown. Thrombotic device 114 may be a gel-coated stent, a thrombotic material, such as putty, in particular Onyx™ putty, or PTFE in a solid form or any other non-absorbable material for creating an immobile thrombus in the vein.

Figure 7:
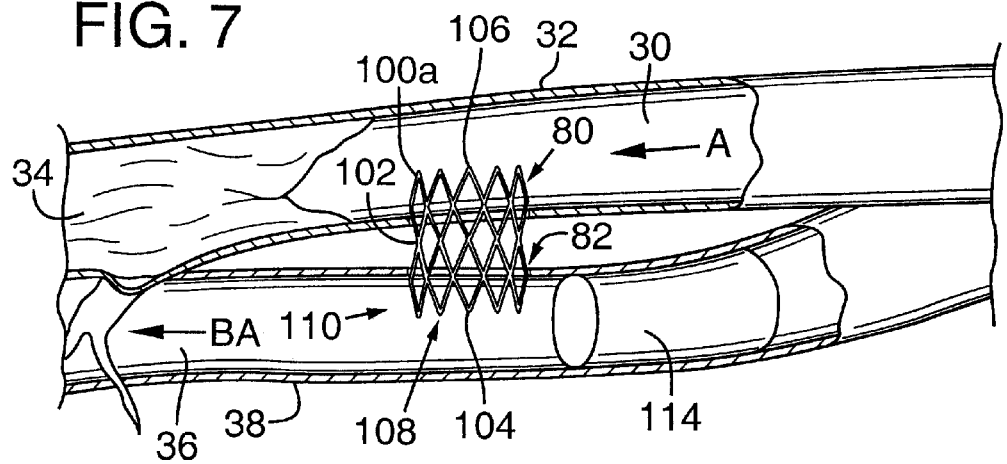
FIG. 7 is a cross-sectional view of an artery and a vein with a fistula therebetween, the fistula maintained by a perpendicularly-disposed stent that expands in cross-section and contracts in length to a broader, shorter dimension than the angularly-extending stent of the embodiment depicted in FIG. 6.

As shown in FIG. 7, a shorter stent 100a may alternatively be inserted through openings 80, 82 that does not prevent venous blood flow in vein 36, in conjunction with thrombotic device 114. Stent 100a is also shown in an attitude roughly perpendicular to artery 30 and vein 36, illustrating that the creation of the fistula may be done from artery to vein, as described above, or from vein to artery, and with the catheters inserted from either direction with respect to blood flow, within the scope of the present invention.

Figure 8:
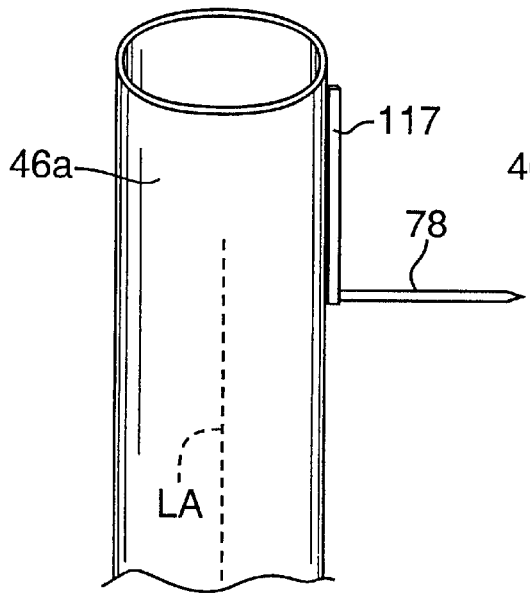
FIG. 8 is an isometric view of an alternative embodiment of the arterial catheter with the needle for creating the opening through the vein and artery walls, the needle in this embodiment installed externally on the arterial catheter, the needle having a nominal, inactive position flush alongside the catheter, generally parallel to the longitudinal axis of the catheter, and shown in a deployed, active configuration at an angle to the longitudinal axis of the catheter, the angle as shown in FIG. 8 being about 90°.
Figure 9:
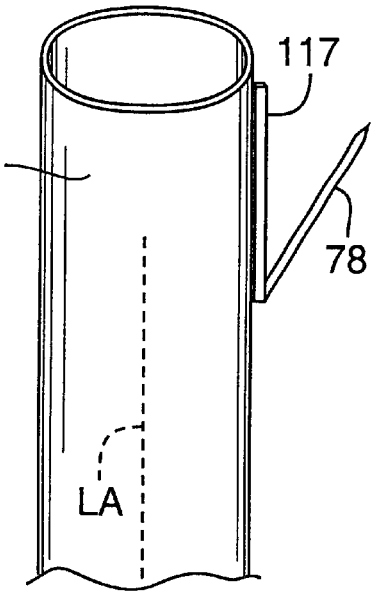
FIG. 9 is an isometric view of an alternative embodiment of the arterial catheter similar to that shown in FIG. 8, the needle in this embodiment shown in the deployed, active configuration at an angle to the longitudinal axis of the catheter of about 30°.

FIGS. 8 and 9 show an alternative embodiment for the tool to create the openings in artery wall 32 and vein wall 38. In this embodiment, needle 78 is mounted externally on arterial catheter 46a, and the physician can selectively position needle 78 either in the inactive configuration flush with a housing 117 on the outer surface of the catheter, or deploy needle 78 in the active configuration. FIG. 8 shows needle 78 in the active configuration at an angle of about 90° with respect to axis LA of arterial catheter 46. FIG. 9 shows the needle in the active configuration at an angle of about 30° with respect to axis LA of arterial catheter 46a. It will be understood that control of needle 78 may be setup so that the physician can maneuver needle 78 between the inactive configuration and a single active angle, or alternatively to any desired angle relative to the arterial catheter. Needle 78 in the inactive configuration is generally parallel with longitudinal axis LA of arterial catheter 46a.

Single-lumen arterial catheter 46a in the embodiment shown in FIGS. 8 and 9 may alternatively be replaced with three-lumen catheter 46 of FIGS. 2 and 3, and needle 78, which, as noted above, may be hollow, may have sharp-tipped wire 88 inserted therethrough. Wire 88 may include a magnetic tip 90 attracted to corresponding magnets on venous catheter 44, which directs tip 90 towards vein 36 when both catheters are adjacent the fistula site to facilitate creating openings 80, 82. Alternatively, wire 88 can be a radio-frequency wire of the type described in U.S. Pat. Nos. 5,743,900 and 6,190,379, both of which are hereby incorporated by openings 80, 82 through the artery and the vein.

Figure 10:
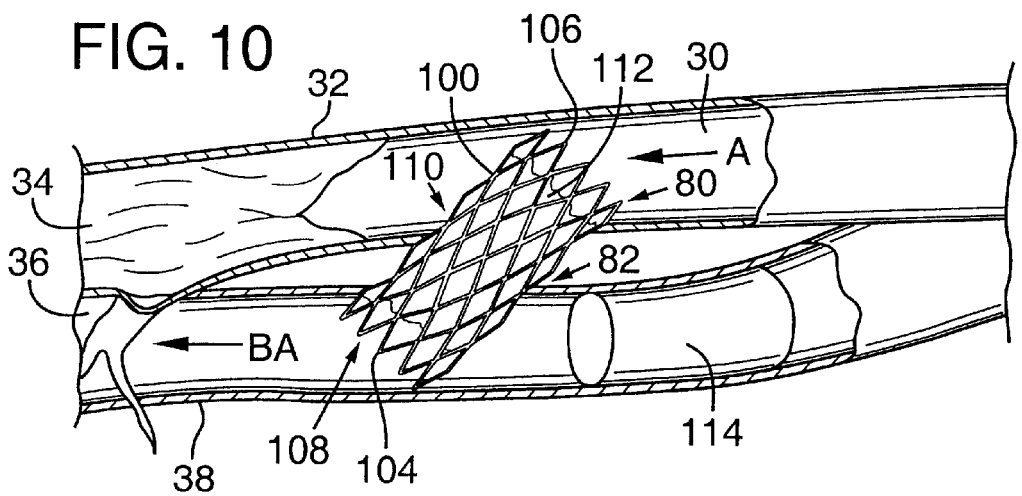
FIG. 10 is a partial cross-sectional view showing the artery and vein and the stent of FIG. 6 with a thrombotic coating on the frame of the stent to prevent blood leakage.

As shown in FIG. 10, stent frame 102 may be covered with a non-absorbable material 112, such as Dacron™, PTFE, thrombotic jell or putty, and the-stent may thus prevent venous blood flow proximal to the fistula. If the stent is appropriately oriented in the vein and artery and of sufficient size, and the non-absorbable material as assisted by the clotting of additional blood on the stent provides a completely solid passageway, the stent will prevent venous blood flow proximal to the fistula site. However, as illustrated in FIG. 10, there may be openings in stent frame 102, and thus thrombotic device 114 may be inserted into vein 36 to create a complete block.

Previously known stents, typically cylindrical in shape, have been used to maintain an opening in a partially clogged or otherwise constricted passageway, such as an artery. Stents used for this purpose typically have been self-expanding, i.e., they are formed of a material having "memory" in a particular configuration. The stents can be mechanically compressed to a slightly narrowed, lengthened configuration for insertion into the clogged artery. When released from the compressed configuration, the stents expand in cross-section and shorten slightly to maintain a passageway through the artery. For such uses, the expansion of the stent provides the beneficial maintenance of the passageway, while the shortening reduces the effective length of the stent, a generally undesirable characteristic in previous stents.

Figure 11:
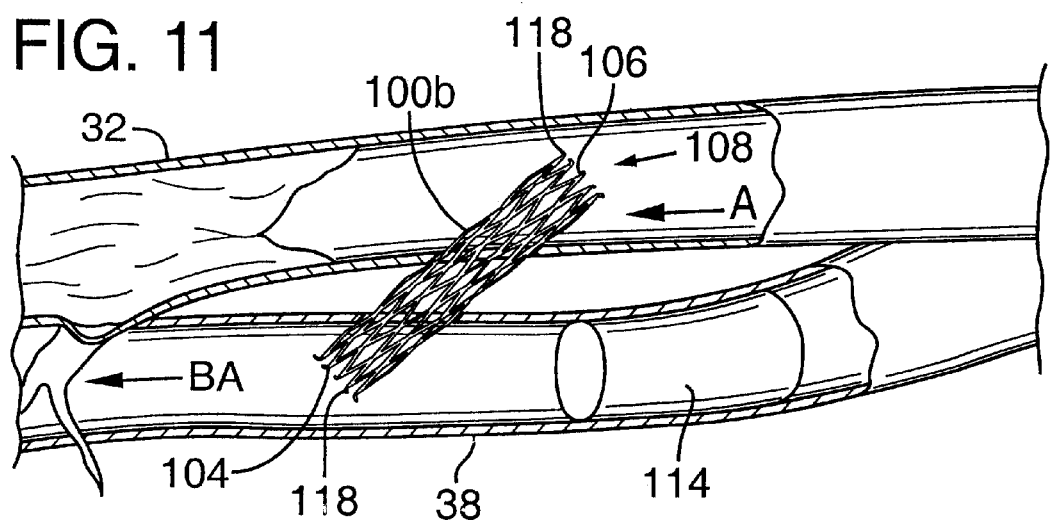
FIG. 11 is a partial cross-sectional view showing the artery and the vein and a side view of the stent as it would be positioned and compressed in an insertion device just prior to installation at a position extending through the openings in the artery and the vein, the stent including hooks on the end struts of the frame and being shown in a mechanically compressed state wherein the stent is much longer and narrower Man a nominal state.
Figure 12:
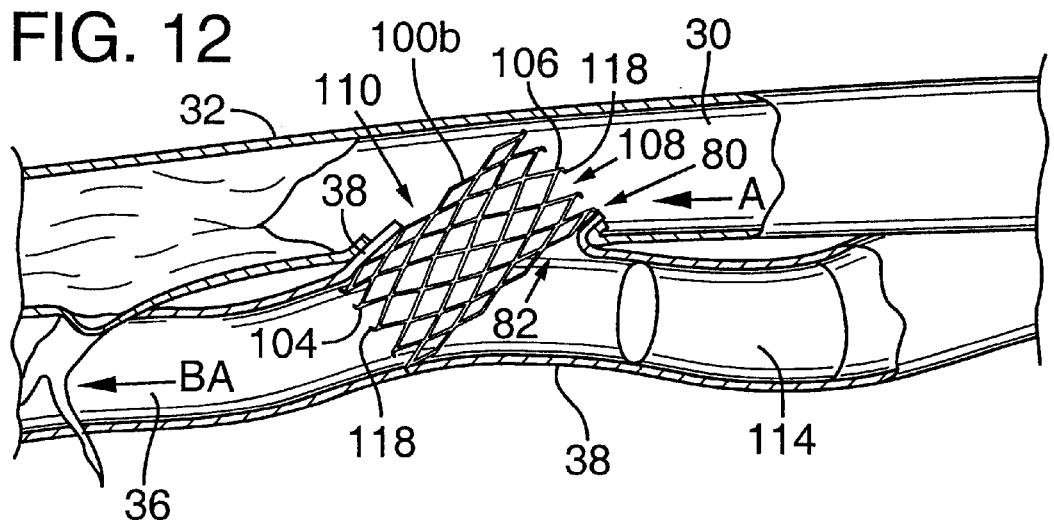
FIG. 12 is a partial cross-sectional view including a side view of the stent of FIG. 11, the stent now shown in its nominal state that is much broader and shorter than that of FIG. 11 and the hooks embedded in the inner wall of the artery and the vein and pulling the wall of the vein into the artery.

In the present invention, as shown in FIGS. 11 and 12, a stent 100b for maintaining fistula 110 includes small hooks 118 at open ends 104 and 106 of frame 102 that are configured to embed in artery and vein walls 32 and 38. Stent 100b is designed to pull together two separate tissues in a manner not contemplated with previous stents. Hooks 118 pull vein wall 38 and artery wall 32 tightly together, even invaginating vein wall 38 into opening 80 in artery wall 32, thus providing a seamless connection between the vein and the artery without blood leakage into the surrounding area. The self-expanding stent replaces or augments the function of the balloon angioplasty, enlarging openings 80, 82 for adequate passage of blood therethrough.

Stent 100b, which is typically cylindrical in cross-section may have a nominal diameter of about 5 mm, corresponding to a cross-sectional area of about 19.6-mm$^2$, and can be compressed to a diameter of about 1-mm to 1.5-mm, corresponding to a cross-sectional area of about 0.785-mm$^2$ to 1.77-mm$^2$. Thus, the ratio of the cross-sectional area of stent 100b in the nominal configuration to the cross-sectional area in the compressed configuration ranges from about 25.0 down to about 11.1, and the corresponding ratio of diameter ranges from about 5.0 down to about 3.33. The nominal length of stent 100b typically is from about 5-mm to about 8-mm, while the compressed length typically is from about 10-mm to about 20-mm. These dimensions and ratios may be altered and selected to fit the configuration of the artery and vein adjacent the fistula site.

Stent 100b is shown schematically in FIG. 11 in the position and configuration in which it would be placed by an insertion catheter, which is not shown. The insertion catheter may be a single lumen catheter, or the three-lumen catheter 46. In either case, stent 100b compressed is within a catheter lumen, and the catheter includes a control for the physician to eject stent 100b when it is in the appropriate position. As stent 100b is ejected from the catheter, typically with the vein end emerging first and while the catheter is simultaneously withdrawn, the stent begins to expand in cross-section, and hooks 118 in vein 36 embed in the inner surface of vein wall 38. As stent 100b is further ejected it contracts in length, and embedded hooks 118 pull vein wall 38 toward artery 30. Once fully ejected, as shown in FIG. 12, hooks 118 embed in the inner surface of artery wall 32, pulling artery wall 32 towards vein 36. The inner surface of the vessel wall in which the hooks are first embedded tends to invaginate into the opening of the other vessel, as shown for vein wall 32 into arterial opening 80 in FIG. 12, thus creating a leak-free fistula between the vessels. Alternatively, the fistula may be created by multiple pairs of openings between the artery and the vein, and the openings connected by multiple stents.

FIGS. 13–15 show an alternative embodiment for venous-expansion catheter 44, including a wire basket 120 deployable adjacent distal end 50 of catheter 44. Wire basket 120 can be compressed within distal end 50 of catheter 44 while catheter 44 is guided to the fistula site, and when deployed, the wire basket expands radially with sufficient force to extend outwardly wall 38 of vein 36 towards contact with artery wall 32. Wire basket is shown as formed of four limbs, but other numbers of limbs may be used, e.g., six or eight. The maximum force of expansion for any particular wire basket 120 may be set by the nominal dimensions of the basket and may be adjusted by the physician during the operation, e.g., by adjusting the extent to which the basket is deployed beyond distal end 50. Wire basket 120 can dilate the vein typically about 3-mm to about 10-mm, or, if necessary, as much as about 15-mm.

Wire basket 120 may be made of a radiopaque material, or may include one or more radiopaque markers 122 positioned to allow radiographic determination of the position and expansion of the basket, e.g., at the fore and aft ends of the basket and the midpoints of each limb. The physician can observe radiographically basket 120 or markers 122 to judge the position and efficacy of the expansion of vein 36.

Wire basket 120 is typically coupled to a wire, such as wire 62 of FIGS. 1–3 inserted through one of the lumens in venous catheter 44 and wire 62 is controllable by the physician in position relative to catheter 44 to control deployment of basket 120. As with the embodiment shown in FIGS. 1–3, arterial catheter 46 of catheter apparatus 32 includes a distal end 66 that the physician inserts into artery 30 and positions adjacent arterial fistula site 54. The physician creates openings 80, 82 in the artery and vein walls as for the previous embodiment, except that wire basket 120 will maintain its shape and the expansion of the vein walls without concern for potential puncture and deflation of a balloon. Wire basket 120 may include one or more magnets, or other magnetically-attracted material cooperating with one or more magnets, or other magnetically-attracted material on arterial catheter 46, needle 78 or wire 88 to urge the basket and the catheter, needle, or wire toward one another.

FIGS. 16–19 show another embodiment of the present invention wherein the radially expandable structure of venous catheter 44 includes two balloons 124, 126 longitudinally spaced along distal end 50 with an injection port 128 between the balloons. Balloons 124, 126 are shown inflated, in FIG. 16, creating an isolated area 130 in the vein between the balloons and expanding outwardly vein wall 38 adjacent fistula site 40. The balloons typically are inflated with a solution containing a contrast, and/or the catheter includes radiopaque markers, allowing the physician to gauge the position of the balloons before, during, and after inflation. As shown in FIG. 17, a solution 132, also including a contrast, may be pumped into isolated area 130 through injection port 128 under sufficient pressure to cause vein wall 38 further to extend outwardly toward contact with artery wall 32. The physician may check the extension of vein wall 38 by radiographically observing the contrast in solution 132.

The embodiment of FIGS. 16–19 is similar to that of FIGS. 1–3 for creating openings 80, 82 in the artery and vein walls: the physician inserts arterial catheter 46 into artery 30 and distal offset tip 76 is pointed at arterial fistula site 54. As shown in FIGS. 18 and 19 the tool for creating openings 80, 82 in the artery and vein walls is sharp-tipped wire 88. As wire 88 creates opening 82 in vein wall 38, vein 32 generally maintains the expanded shape because the sharp-tipped wire enters into isolated area 130, rather than either of balloons 124, 126. Balloons 124, 126 can then be deflated and withdrawn, and wire 88 further extended into vein 32, as shown in FIG. 19. A balloon catheter and/or a stent may be maneuvered through the openings, as described above for FIGS. 5 and 11–12 respectively.

FIGS. 20 and 21 show an alternative embodiment for providing the inactive and active configurations, respectively, for needle 78. In this embodiment, needle 78 is hollow and terminates in a beveled, pointed tip 134, and is typically coupled to arterial catheter 46 in a fixed relative position beyond distal end 66 of catheter 46. That is, needle 78 is not made inactive by retraction into distal end 66 of catheter 46. Instead, wire 74 terminates in a generally blunt distal end 136, and to provide the inactive configuration, as shown in FIG. 20, wire 74 is inserted through needle 78 to a position at least flush with needle tip 134 wherein tip 134 cannot causes trauma to vessel walls. As shown in FIG. 21, the active configuration is provided by withdrawing wire 74 from needle tip 134, so that tip 134 can create the desired openings through the artery and vein walls as described above.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also included within the subject matter of the inventions of the present disclosure.

I claim:

1. A catheter apparatus for arterializing a vein by creating a fistula between the vein and an artery, the apparatus comprising:
    an arterial catheter having a distal end insertable to a position wherein the distal end is adjacent a site within the artery for the fistula,
    a venous catheter having a distal end insertable to a position wherein the distal end is adjacent a site within the vein for the fistula, the venous catheter including a radially expandable structure adjacent the distal end which selectively extends outwardly a portion of the wall of the vein adjacent the venous fistula site towards contact with the wall of the artery adjacent the arterial fistula site, a tool for creating an opening through the wall of the artery adjacent the arterial fistula site and an opening through the outwardly extending portion of the wall of the vein adjacent the venous fistula site, wherein the radially expandable structure of the venous catheter includes a wire basket deployable adjacent the distal end of the venous catheter, the wire basket being expandable with sufficient force to extend outwardly the wall of the vein towards contact with the arterial wall.

2. The catheter apparatus of claim 1 wherein the wire basket includes a radiopaque marker.

3. A catheter apparatus for arterializing a vein by creating a fistula between the vein and an artery, the apparatus comprising:

an arterial catheter having a distal end insertable to a position wherein the distal end is adjacent a site within the artery for the fistula, a venous catheter having a distal end insertable to a position wherein the distal end is adjacent a site within the vein for the fistula, the venous catheter including a radially expandable structure adjacent the distal end which selectively extends outwardly a portion of the wall of the vein adjacent the venous fistula site towards contact with the wall of the artery adjacent the arterial fistula site, and a tool for creating an opening through the wall of the artery adjacent the arterial fistula site and an opening through the outwardly extending portion of the wall of the vein adjacent the venous fistula site, wherein the tool includes a needle coupled to the arterial catheter adjacent the distal end of the arterial catheter, the needle being selectively switchable between a first, inactive configuration wherein the needle can be guided through the artery without causing trauma to the artery wall and a second, active configuration wherein the needle is operative to create the opening in the artery wall, and wherein the needle is hollow and terminates in a beveled, pointed tip, and wherein the tool further includes a wire selectively insertable through the needle, the wire having a generally blunt distal end, the wire and needle providing the inactive configuration when the distal end of the wire extends through the needle to a position at least flush with the needle tip, and the wire and needle providing the active configuration when the wire is retracted from the needle tip.

4. A catheter apparatus for arterializing a vein by creating an opening in the vein wall and an opening in an arterial wall, and developing a fistula between the vein and the artery, the apparatus comprising:

an arterial catheter having a distal end insertable to a position adjacent a site within the artery for the fistula, a venous catheter having a distal end insertable to a position adjacent a site within the vein for the fistula, the venous catheter including a wire basket adjacent the distal end of the venous catheter, the wire basket selectively deployable to extend the wall of the vein outwardly towards contact with the wall of the artery, and a tool for creating an opening through the wall of the artery and an opening through the wall of the vein adjacent the sites for the fistula.

5. The catheter apparatus of claim 4 further comprising a first magnet disposed on the wire basket and a second magnet disposed on the distal end of the arterial catheter, the magnets configured for mutual attraction to urge the wire basket and the distal end of the arterial catheter toward one another.

6. The catheter apparatus of claim 4 wherein the arterial catheter includes a body defining a longitudinal axis, the arterial catheter further including a distal tip that is selectively switchable between a first configuration wherein the tip is offset from the longitudinal axis by at least about 30°, and a second configuration wherein the distal tip aligns generally with the longitudinal axis.

7. The catheter apparatus of claim 6 further comprising a stiffening wire insertable through the arterial catheter, wherein the distal tip of the arterial catheter is nominally in the first configuration and is selectively switchable to the second configuration by insertion of the stiffening wire through the arterial catheter to a position adjacent the distal tip.

8. The catheter apparatus of claim 4 wherein the tool includes a wire having a sharp tip, the wire insertable through the arterial catheter for deployment of the sharp tip adjacent the distal end of the arterial catheter, and wherein at least one of the wire basket and the sharp wire includes a magnet, and the other one of the wire basket and the sharp wire includes magnetically-attracted material.

9. The catheter apparatus of claim 8 wherein the wire includes a magnet disposed adjacent the tip, and wherein the wire basket includes a magnet, the magnets arranged for mutual attraction between the wire and the basket.

10. The catheter apparatus of claim 4 wherein the venous catheter includes a first lumen defined therethrough for receiving the wire basket, a second lumen defined therethrough for injection of a contrast adjacent the distal end of the venous catheter, and a third lumen for receiving a guidewire.

11. The catheter apparatus of claim 4 wherein the wire basket includes a radiopaque marker.

12. The catheter apparatus of claim 4, wherein the tool includes a needle for creating the openings through the walls of the artery and the vein, the needle providing a selectable inactive configuration, and a selectable active configuration for creating the openings.

13. The catheter apparatus of claim 12, wherein the needle is installed adjacent the distal end of the arterial catheter, and the needle is within the distal end in the inactive configuration, and the needle extends beyond the distal end in the active configuration.

14. The catheter apparatus of claim 12, wherein the needle is installed extending beyond the distal end of the arterial catheter, the needle pointing generally straight out from the catheter in the inactive configuration, and the needle disposed at an angle of at least about 30° with respect to a longitudinal axis of the arterial catheter.

15. The catheter apparatus of claim 4 wherein the arterial catheter defines a lumen and the tool includes a sharp wire configured for insertion through the lumen, the wire further configured to be deployed beyond the distal end of the arterial catheter to create the openings in the walls of the artery and the vein.

16. The catheter apparatus of claim 4 further including an embolization catheter for depositing an embolization device at a location in the vein proximal to the fistula.

17. The catheter apparatus of claim 4 further including a stent for connecting the artery and the vein at the fistula.

18. The catheter apparatus of claim 17 wherein the stent includes a frame defining a cross-sectional area, the stent expandable to increase the cross-sectional area by a factor of at least about 10.

19. The catheter apparatus of claim 17 wherein the stent includes a plurality of hooks configured to embed in at least one of the artery and the vein walls.

20. The catheter apparatus of claim 17 wherein the stent includes a plurality of hooks configured to embed in the artery wall and in the vein wall.

21. The catheter apparatus of claim 4 wherein at least one of the arterial catheter and the venous catheter includes at least three lumens.

22. The catheter apparatus of claim 4 wherein the arterial catheter includes a body defining a longitudinal axis and a distal tip that is selectively switchable between a first configuration generally parallel to the longitudinal axis and a second configuration offset from the longitudinal axis by at least about 60°.

23. A method of arterializing a peripheral vein by creating a fistul a between the vein and a peripheral artery, the method comprising:

providing an arterial catheter having a distal end and inserting the arterial catheter into the artery to a position wherein the distal end is adjacent a site for the fistula within the artery;

providing a venous catheter having a distal end and inserting the venous catheter into the vein to a position wherein the distal end is adjacent a site for the fistula within the artery;

after positioning the arterial and venous catheters, radially expanding a portion of the vein wall adjacent the venous fistula site to bring the venous fistula site in closer proximity to the arterial fistula site;

after radially expanding the portion of the vein wall, creating an opening through the wall of the artery adjacent the arterial fistula site and creating an opening through the wall of the vein adjacent the venous fistula site, wherein the venous catheter includes a wire basket deployable adjacent the distal end of the venous catheter, and wherein the step of radially expanding a portion of the vein wall includes deploying the wire basket.

24. The method of claim 23 wherein the wire basket includes a radiopaque marker and further comprising the step, before creating the openings in the vein and artery walls, of radiographically observing the position of the marker.

25. The method of claim 23, further comprising the steps of providing a stent and depositing the stent through the openings in the walls of the artery and the vein to form a passageway between the artery and the vein.

26. The method of claim 25, wherein the stent includes a plurality of hooks configured to embed in at least one of the artery wall and the vein wall.

27. The method of claim 23, wherein the vein includes a valve distal of the fistula, and further including the steps of providing a cutting device, and inserting the cutting device into the vein and excising at least a portion of the valve.

* * * * *